(12) United States Patent
Cunliffe et al.

(10) Patent No.: US 8,337,506 B2
(45) Date of Patent: Dec. 25, 2012

(54) COMBINATION BONE FIXATION DEVICE AND BENDING TOOL

(76) Inventors: Mark Richard Cunliffe, Huddersfield (GB); Malcolm Graham Ness, Morpeth (GB)

( * ) Notice: Subject to any disclaimer, the term of this patent is extended or adjusted under 35 U.S.C. 154(b) by 1317 days.

(21) Appl. No.: 11/940,540

(22) Filed: Nov. 15, 2007

(65) Prior Publication Data

US 2008/0294165 A1  Nov. 27, 2008

Related U.S. Application Data

(63) Continuation-in-part of application No. PCT/GB2007/001912, filed on May 21, 2007.

(51) Int. Cl.
*A61B 17/80* (2006.01)
*A61B 17/58* (2006.01)

(52) U.S. Cl. .......................... 606/101; 606/283; 606/284

(58) Field of Classification Search .................. 606/101, 606/283–285
See application file for complete search history.

(56) References Cited

U.S. PATENT DOCUMENTS

| | | | |
|---|---|---|---|
| 4,905,679 A | | 3/1990 | Morgan |
| 5,336,224 A | * | 8/1994 | Selman .......................... 606/280 |
| 5,389,099 A | * | 2/1995 | Hartmeister et al. ........ 606/86 A |
| 6,004,353 A | | 12/1999 | Masini |
| 6,423,068 B1 | | 7/2002 | Reisberg et al. |
| 6,821,279 B2 | * | 11/2004 | Di Emidio .................... 606/285 |
| 7,229,446 B2 | * | 6/2007 | Capanni ........................ 606/86 R |
| 7,740,634 B2 | * | 6/2010 | Orbay et al. .................. 606/101 |
| 2004/0111089 A1 | | 6/2004 | Stevens et al. |
| 2004/0236327 A1 | | 11/2004 | Paul et al. |
| 2005/0015090 A1 | | 1/2005 | Silverman |
| 2005/0261780 A1 | | 11/2005 | Heino et al. |

FOREIGN PATENT DOCUMENTS

| | | |
|---|---|---|
| EP | 0491983 | 7/1992 |
| GB | 2125295 | 3/1984 |
| GB | 2405342 | 3/2005 |
| WO | 9905982 | 2/1999 |
| WO | 0040167 | 7/2000 |
| WO | 2005122965 | 12/2005 |

OTHER PUBLICATIONS

Partial International Search Report for PCT/GB2007/001912, dated Nov. 30, 2007.
Search Report for Application No. GB0610630.6 dated Nov. 27, 2006.
Search Report for Application No. GB0709693.6 dated Aug. 24, 2007.

* cited by examiner

*Primary Examiner* — Alvin Stewart
*Assistant Examiner* — Julianna N Harvey
(74) *Attorney, Agent, or Firm* — Howard & Howard Attorneys PLLC

(57) ABSTRACT

A combination of bone fixation device and bending tool. The bone fixation device comprising a plurality of screw receiving members. Each screw receiving member having an aperture extending there through for receiving a screw. The screw receiving members being connected together in a line by plastically deformable connecting arms extending therebetween. The bending tool comprising first and second bending arms. Each bending arm comprising a first face, a second face and a side wall extending therebetween. The side wall comprising a recess extending between the first and second faces. The intersection of the recess with the first and second faces defining first and second connecting arm receiving apertures respectively. The recess being adapted to receive a screw receiving member.

8 Claims, 9 Drawing Sheets

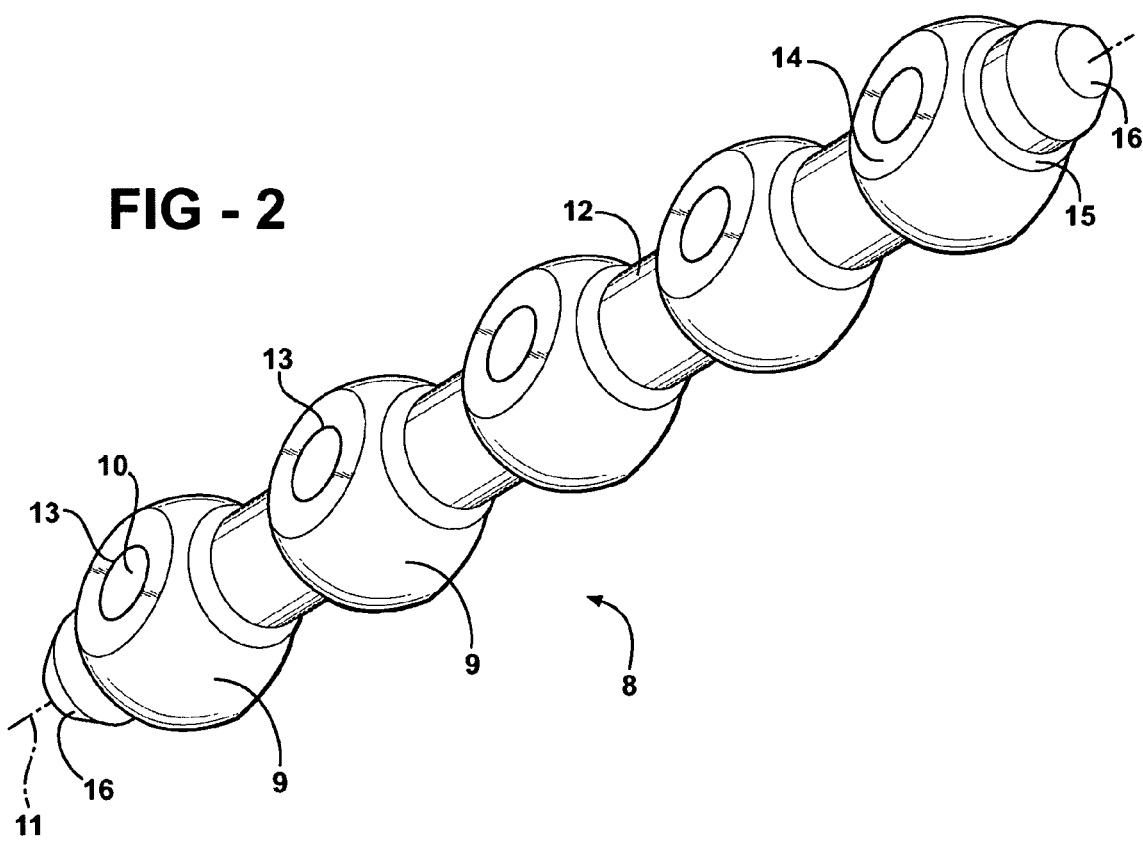

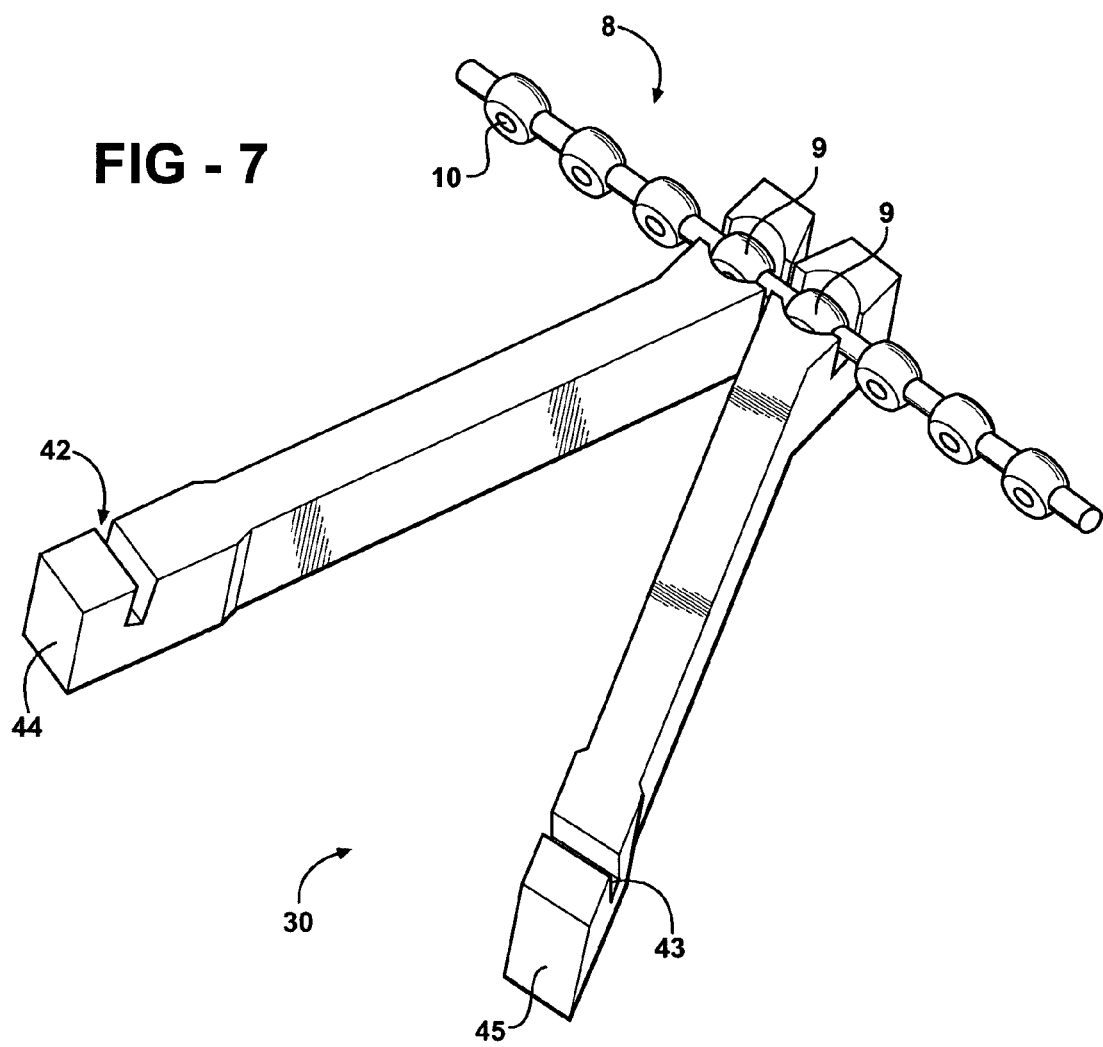

COMBINATION BONE FIXATION DEVICE AND BENDING TOOL

The subject patent application is a continuation-in-part of co-pending International Application No. PCT/GB2007/001912, which was filed on 21 May 2007 with the World Intellectual Property Organization.

The present invention relates to a combination of bone fixation device and bending tool. More particularly, but not exclusively, the present invention relates to a combination of a bone fixation device and a bending tool, the bone fixation device comprising a plurality of screw receiving members and the bending tool comprising two bending arms, each arm having a recess for receiving a screw receiving member.

Bone fixation devices are known. Such devices typically comprise a plastically deformable plate such as a metal plate. A plurality of screw receiving apertures extend through the plate. In use the plate is positioned against a bone and screws passed through the apertures to fix the plate to the bone.

More complex bone fixation devices are also known. U.S. Pat. No. 5,336,224 discloses a bone fixation device comprising a plurality of screw receiving members, each having a screw receiving aperture extending there through. The screw receiving members are connected together in a line by connecting arms.

In order to ensure a close fit between the device and the bone it is often necessary to deform the device slightly. This is typically done by gripping the device at opposite ends and bending it. The device deforms at its weakest points which is usually around the screw receiving apertures. This deforms the apertures, reducing the accuracy of the fit between the apertures and screws. This allows the device to move relative to the bone during use.

The combination according to the invention seeks to overcome this problem.

Accordingly, the present invention provides a combination of bone fixation device and bending tool. The bone fixation device comprises a plurality of screw receiving members. Each screw receiving member having an aperture extending there through for receiving a screw. The screw receiving members being connected together in a line by plastically deformable connecting arms extending therebetween. The bending tool comprising first and second bending arms. Each bending arm comprising a first face, a second face and a side wall extending therebetween. The side wall comprising a recess extending between the first and second faces. The intersection of the recess with the first and second faces defining first and second connecting arm receiving apertures respectively. The recess being adapted to receive a screw receiving member.

The bending tool can be employed to bend the bone fixation device without deforming the portion of the bone fixation device around the screw receiving apertures. A surgeon can therefore use the bending tool to deform the bone fixation device to the desired shape and still obtain a good fit between the bone fixation device and bone screws.

Preferably, the recess in the side wall of each bending arm is arranged proximate to an end of the bending arm.

At least one of the bending arms can have a bend along its length.

The screw receiving members can be spherical.

Preferably a long axis extends between the screw receiving members, the outer surface of the screw receiving members being asymmetric about the long axis.

The screw receiving members can be frusto-spherical, having a flattened portion around at least one mouth of the screw receiving aperture.

The screw receiving members can have flattened portions around both mouths of the screw receiving apertures.

Preferably, the flattened portions define two spaced apart parallel surfaces.

Preferably, the side wall of each bending arm comprises a slot extending between the first and second faces, each slot being adapted to receive a screw receiving member in a first orientation and to prevent rotation of the screw receiving member relative to the slot about the long axis.

Preferably, each of the slots extends into its arm at an angle to the normal to the side wall.

Preferably, the slot in the first bending arm is inclined at a different angle to the normal to the side wall to the slot in the second bending arm.

The slots can have parallel side walls.

In a further aspect of the invention there is provided a method of connecting a bone fixation device to a bone utilizing screws and a bending tool with the bone fixation device having a plurality of screw receiving members and the bending tool having first and second bending arms with each bending arm defining a recess. The method comprises the steps of:

deforming the bone fixation device to a desired profile by means of the bending tool; and, screwing the bone fixation device to the bone by means of screws inserted through the screw receiving members;

the step of deforming the bone fixation device comprising the steps of:

(a) selecting two screw receiving members of the bone fixation device and arranging one in each recess of the two bending arms of the bending tool;

(b) displacing the arms of the bending tool to bend the bone fixation device; and, (c) repeating steps (a) and (b) until the bone fixation device is the desired profile.

Preferably, the two screw receiving members are adjacent screw receiving members.

The step of deforming the bone fixation device can further comprise (a) selecting two screw receiving members of the bone fixation device and arranging the one in each of the slots of the bending arms of the bending tool; and (b) displacing the arms of the bending tool to twist the bone fixation device.

The two screw receiving members can be adjacent screw receiving members.

The present invention will now be described by way of example only and not in any limitative sense with reference to the accompanying drawings in which FIGS. 1A and 1B show a known fixation device before and after deformation;

FIG. 2 shows a bone fixation device of the combination according to the invention in perspective view;

FIG. 7 shows a bending tool and bone fixation device of a combination according to the invention;

Figure 1A:
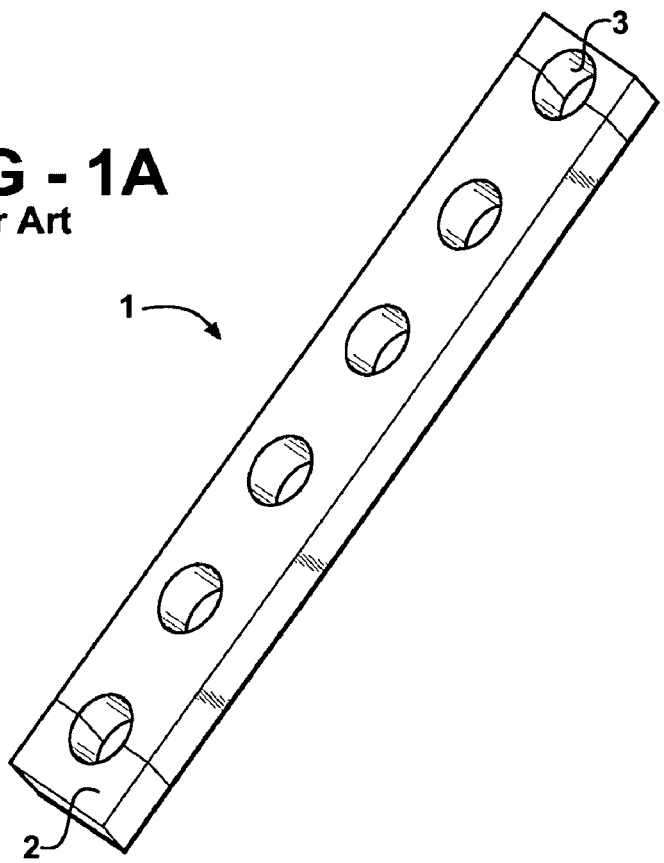
Figure 1B:
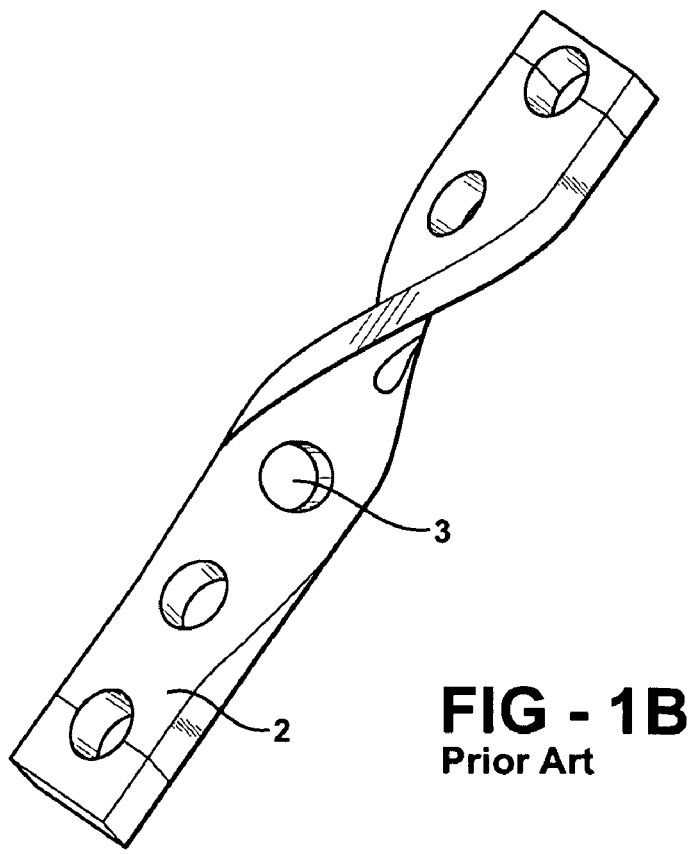

Shown in FIGS. 1A and 1B is a known bone fixation device being a bone plate 1. The bone plate 1 comprises a metal plate 2 having a plurality of apertures 3. In use the bone plate 1 is placed against a bone (not shown). Bone fixation screws (not shown) are passed through the apertures 3 and then screwed into the bone. The screw heads typically engage with the plate 1, firmly fixing the plate 1 in position and preventing it from being displaced with respect to the bone.

A problem can arise however if the bone plate 1 needs to be deformed before it can be fixed to the bone. Deformation of the plate 1 deforms the apertures 3 in the plate 1 as shown. This prevents the screw heads from accurately engaging with the apertures 3 which may result in the plate 1 being free to wobble slightly with respect to the bone. This can reduce the effectiveness of the bone plate 1 as a support for the bone.

In addition, it can be difficult to remove such a known bone plate 1 from the bone when it is no longer required. The screw heads tend to cold weld to the bone plate 1 over time making the screws difficult to remove. It is often necessary to cut the bone plate 1 free which can result in damage to the bone.

Such a known bone plate 1 is also limited as to how it can be deformed. Whilst the plate 1 can be bent as shown in FIG. 1B it is not a simple matter to twist it such that the apertures 3 lie in different planes.

Shown in FIG. 2 is a bone fixation device 8 forming part of the combination according to the invention. The device 8 comprises a plurality of screw receiving members 9. Apertures 10 extend through each of the screw receiving members 9 for receiving screws. A long axis 11 extends between each of the screw receiving members 9. Plastically deformable connecting arms 12 extend along the long axis 11 between the screw receiving members 9 as shown. In this embodiment the long axis 11 passes through the apertures 10 of the screw receiving members 9.

In use the bone fixation device 8 is gripped and bent to the required shape. The arms 12 are more pliable than the screw receiving members 9 and accordingly it is the arms 12 that bend when the force is applied, rather than the screw receiving members 9. The apertures 10 therefore remain undistorted. In addition, in contrast to known bone plates 1 a torsional (twisting) force can be applied to the device 8 rotating one or more of the screw receiving members 9 about the long axis 11 of the device 8 if required. As the long axis 11 passes along the length of the connecting arm 12 the connecting arm 12 twists about its length. The device 8 can therefore be twisted without significantly altering its dimensions. The device 8 can therefore be inserted into small apertures even after twisting.

In this embodiment of the invention each of the screw receiving members 9 is substantially spherical with the apertures 10 extending through the centres of the spheres 9. Each aperture 10 intersects the sphere at mouths 13 on opposite sides of the sphere 9. The sphere 9 comprises a slightly flattened portion 14 around one of the mouths. This reduces the profile of the device 8. It also provides an extended contact area between the screw receiving members 9 and the bone (not shown).

The connecting arms 12 between the screw receiving members 9 are cylindrical. The interface 15 between the arms 12 and spherical screw receiving members 9 is chamfered so that any bending or torsional forces do not concentrate at this interface 15.

The ends 16 of the device 8 are tapered as shown so that the device 8 can be placed between bone and soft tissue without surgically exposing the entire length of bone.

Each of the apertures 10 of this embodiment is cylindrical having a constant area along its length. A portion of the aperture 10 is threaded. The remainder of the aperture 10 is smooth walled.

After bending and/or twisting to the correct shape the device 8 is positioned against the bone. Screws (not shown) are inserted into the apertures 10 through the smooth portions and into threaded engagement with the threaded portions. On further rotation of the screws they penetrate and grip the bone, fixing the device 8 to the bone. A significant advantage of the device 8 is that it can be bent/twisted to the correct shape, positioned correctly and then screws inserted. This considerably simplifies the attachment procedure. As the screw receiving members 9 are aligned with the connection arms 12 along the long axis 11 the device 8 can be twisted about its length without any significant change in dimensions of the device 8. This is particularly useful when inserting the device 8 into small apertures.

The device 8 is adapted to be used with a screw (not shown) having two portions—a threaded portion for gripping the threaded portion of the aperture 10 and then the bone and a smooth portion extending from the threaded portion. The smooth portion has an outer face which is substantially cylindrical and of the same diameter as the threaded portion. The smooth portion is however slightly tapered with its diameter increasing in a direction away from the threaded portion. At its end the diameter of the smooth portion is slightly larger than the diameter of the aperture 10. As the screw is turned and is drawn into the aperture 10 the smooth portion of the screw abuts the smooth portion of the aperture 10 so producing a press fit.

Figure 3:
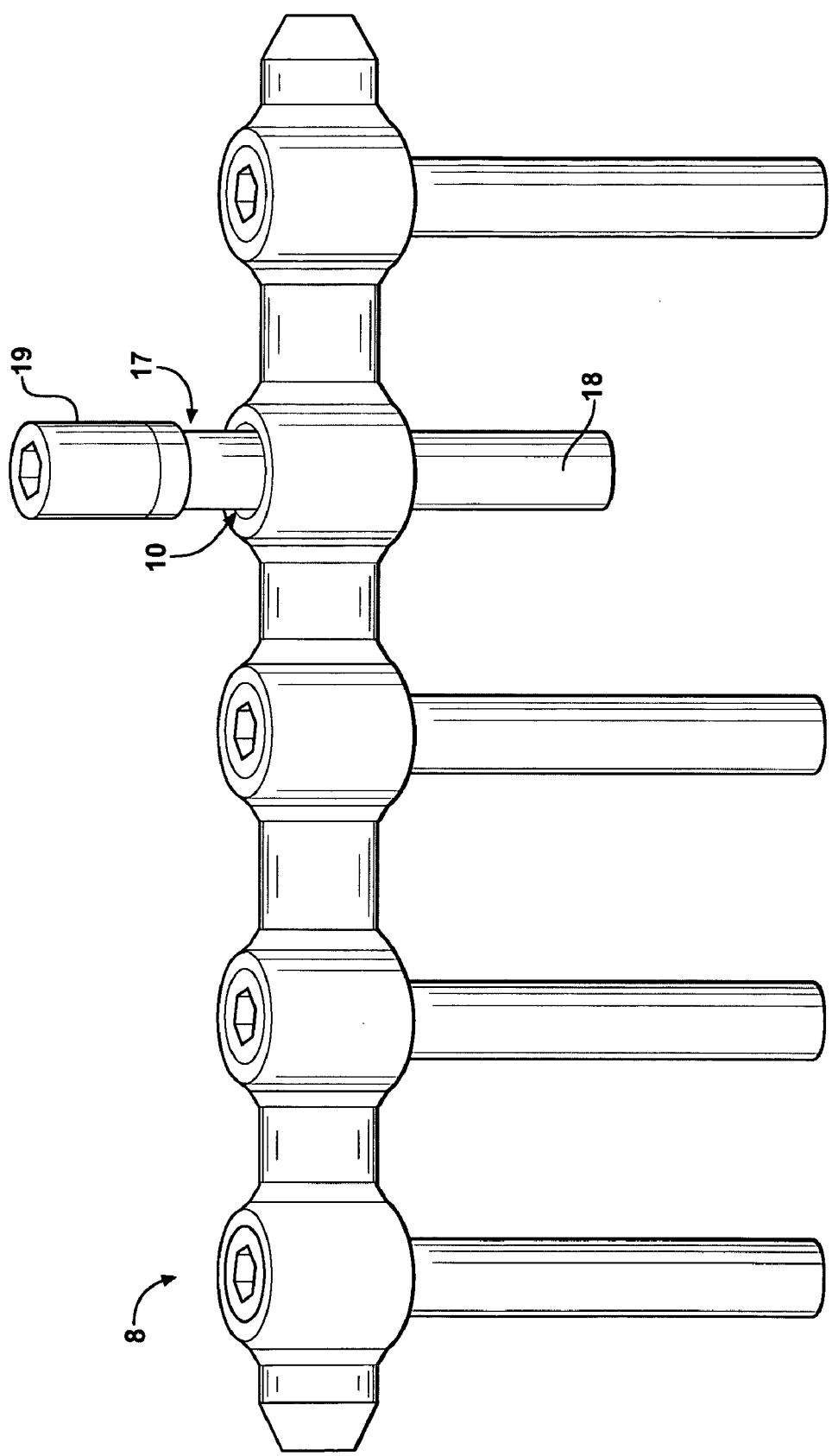
FIG. 3 shows the bone fixation device of FIG. 2 in combination with a screw.

An alternative embodiment of the bone fixation device of the combination according to the invention is shown in FIG. 3. In this embodiment the threaded portion of the aperture 10 is narrower in diameter than the smooth portion. The screw 17 has a narrow threaded portion 18 and a wider smooth tapered head portion 19 as shown. The narrow threaded portion 18 of the screw 17 engages with the narrow portion of the aperture 10 drawing the larger smooth head portion 19 into abutment with the smooth portion of the aperture 10.

The embodiment of FIG. 3 can be used with an alternative design of screw (not shown). The alternative design comprises a threaded shaft having a domed head extending away from the shaft. As the screw is drawn into the aperture 10 the domed head abuts the lip formed by the change in diameter of the aperture 10.

In a further embodiment of the invention (not shown) both the narrow and wide portions of the aperture 10 are threaded. Similarly, the screw comprises a narrow threaded shaft and a larger diameter threaded head. In use the threaded head engages with the larger portion of the aperture 10.

In a further embodiment of the invention (not shown) a portion of the aperture 10 is slightly bevelled so that a standard bone screw head will press fit into engagement with the bevels as the screw is drawn into the aperture 10.

Figure 4:
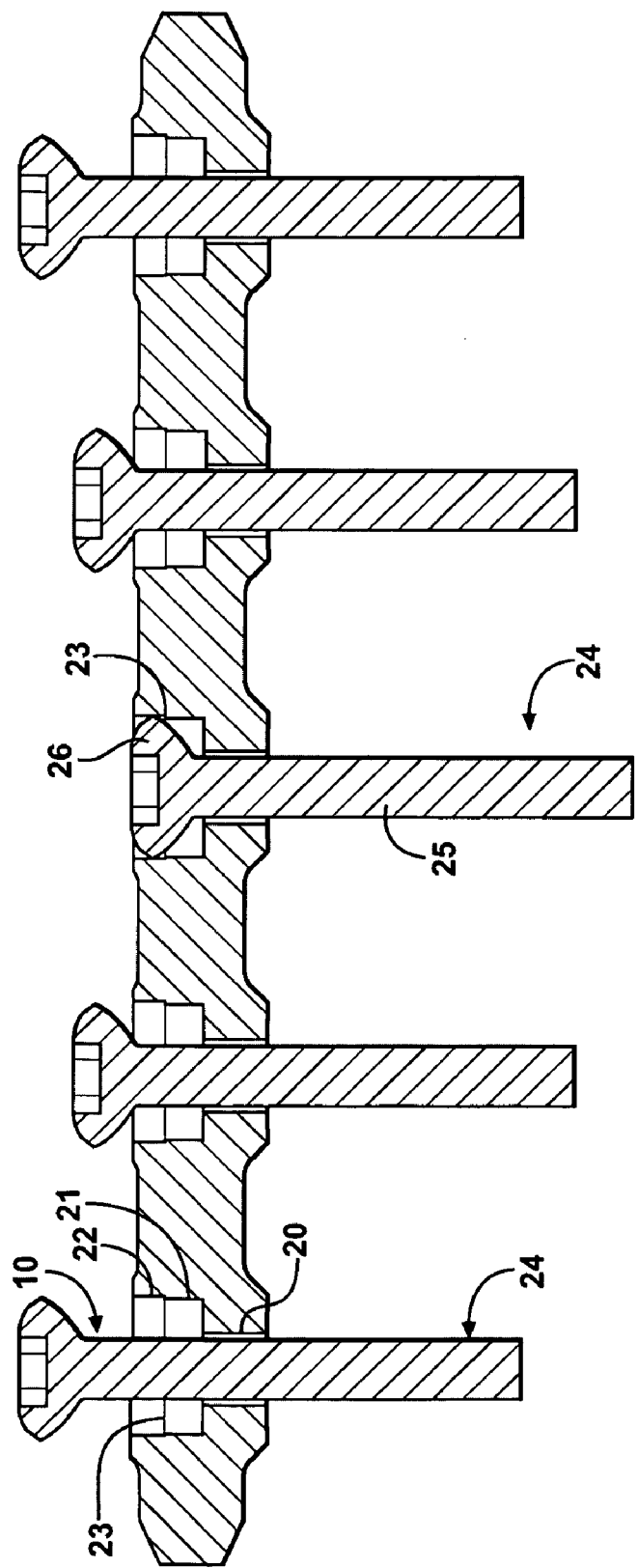
FIG. 4 shows a further embodiment of a bone fixation device of the combination according to the invention in cross sectional view.

Shown in FIG. 4 in cross sectional view is a further embodiment of a bone fixation device 8 of a combination according to the invention. The aperture 10 comprises a first narrow threaded section 20. Extending from this is a second smooth walled section 21 of larger diameter. Extending from the second section 21 is a third smooth walled section 22 of slightly larger diameter then the second section 21. The step change in diameter from the second section 21 to the third section 22 defines a lip 23. In use a screw 24 is inserted into the aperture 10 with the threaded portion 25 of the screw 24 in threaded engagement with the narrower portion 21 of the aperture 10. As the screw 24 is turned and drawn into the aperture 10 the head 26 of the screw 24 abuts the lip 23 producing a tight fit.

Figure 5:
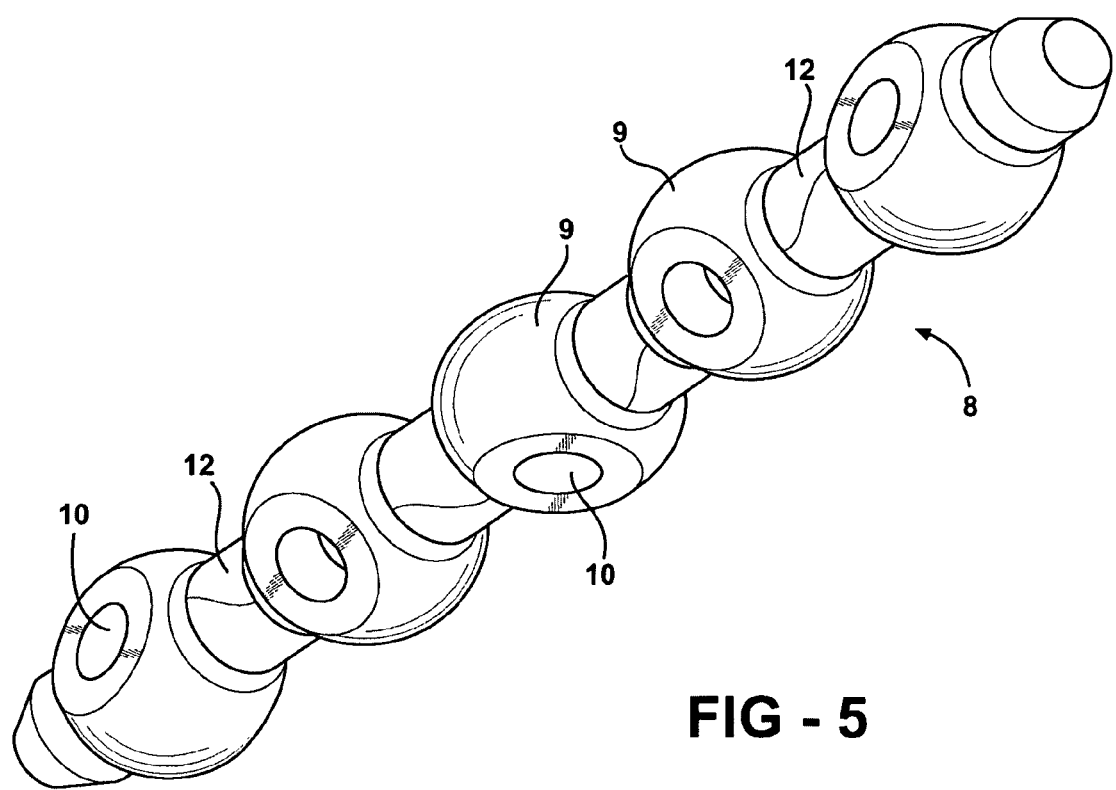
FIG. 5 shows the bone fixation device of FIG. 4 after twisting.

Shown in FIG. 5 is the bone fixation device of FIG. 4 in perspective view. The device 8 has been twisted along its length such that the apertures 10 lie in different planes. As can be seen, the arms 12 have twisted before the screw receiving members 9 deform.

In a further embodiment of the invention the screw receiving members 9 are substantially elliptical.

The device 8 according to the invention can be used with any tool which grips the screw receiving members 9. One preferred embodiment of such a tool comprises jaws having cut out sections which match the spherical component of the screw receiving members 9. The tool also has cut outs which match the interface 15 between the spherical component 9 and connecting arm 12 so that the tool can apply a bending force throughout the length of the bone fixation device 8. In an alternative embodiment the jaws have cut outs which match the flattened portions 14 of the screw receiving members 9.

In use two of the tools are used to grip the screw receiving members 9. The device 8 is then bent and/or twisted to the desired shape and then released.

Bending of a bone fixation device by a bending tool is described in further detail with reference to FIGS. 6 to 9.

Figure 6:
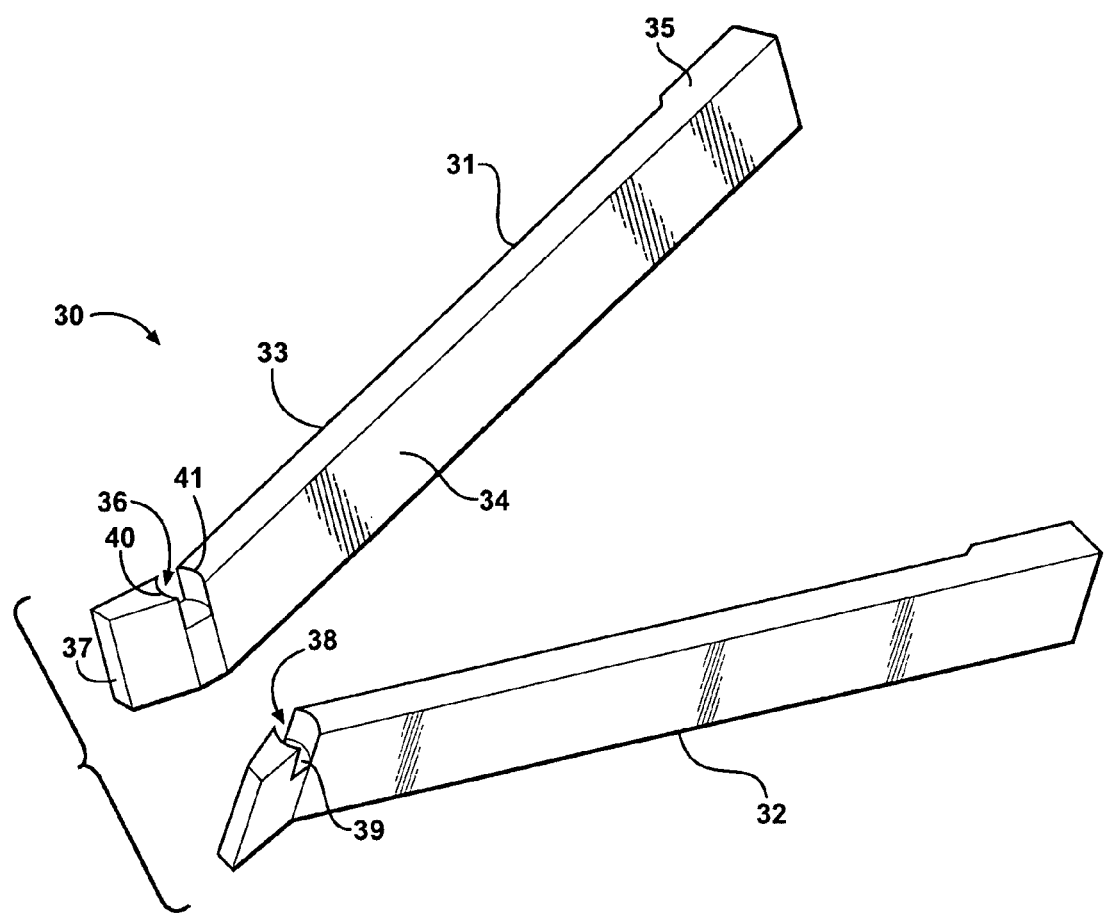
FIG. 6 shows a bending tool of a combination according to the invention.

Shown in FIG. 6 is a bending tool 30 for bending the bone fixation device. The bending tool 30 and bone fixation device 8 together form the combination according to the invention.

The bending tool 30 comprises first and second bending arms 31, 32. Each bending arm 31, 32 has a first face 33, a second face 34 and a side wall 35 extending therebetween. Each of the bending arms 31, 32 is bent along its length as shown.

The side wall 35 of each bending arm 31, 32 comprises a recess 36 proximate to the end 37 of the bending arm 31, 32. The recess 36 extends between the first and second faces 33, 34 as shown. The intersection of the recess 36 with the first and second faces 33, 34 defines first and second connecting arm receiving apertures 38, 39 respectively.

The shape of the recess 36 between the first second connecting arm receiving apertures 38, 39 is defined by side walls 40, 41. The shape of the side walls 40, 41 is complementary to the outer surface of the screw receiving members 9 as is described in further detail below.

Shown in FIG. 7 is a bending tool 30 in combination with a bone fixation device 8. Two adjacent screw receiving members 9 of the bone fixation device 8 are received in the recesses 36 of the bending arms 31, 32 as shown. The connecting arms 12 extend through the connecting arm receiving apertures 38, 39 in the first and second faces 33, 34. The recess 36 is dimensioned so as to be a close fit to the outer surface of the screw receiving members 9. In this embodiment where the screw receiving members 9 are frusto-spherical the side walls 40, 41 of the recess 36 are curved in arcs of approximately constant radius. Typically, the side walls 40, 41 of the recess 36 are curved in the opposite direction proximate to the first and second faces 33, 34. This curvature matches the chamfered interface between the screw receiving members 9 and the connecting arms 12 extending therefrom of the bone fixation device 8. The base of the recess 36 is hemispherical forming a cup shape such that the screw receiving member 9 sits within it. Each of the bending arms 31, 32 of this embodiment of the bending tool 30 further includes a slot 42, 43 remote from the recess 36. The function of these is described in detail with reference to FIGS. 8A, 8B and 9.

The two bending arms 31, 32 are bent along their length such that they diverge in a direction away from the bone fixation device 8. As the two ends 44, 45 of the bending arms 31, 32 remote from the bone fixation device 8 are urged closer together the recesses 36 rotate the screw receiving members 9. This bends the connecting arm 12 between the screw receiving members 9 into a smooth curve as opposed to a 'crease' when conventional bending tools are used. Typically before bending the apertures 10 of the screw receiving members 9 are loaded with tees (not shown) to further minimise distortion of the screw receiving apertures 10.

By moving the bending arms 31, 32 along the bone fixation device 8 one screw receiving member 9 at a time one can deform the bone fixation device 8 to any desired shape in a single plane. More complex deformations in multiple planes are sometimes necessary. The screw receiving members 9 can be rotated in the recesses 36 between bending steps to allow bending in multiple planes.

Figure 8B:
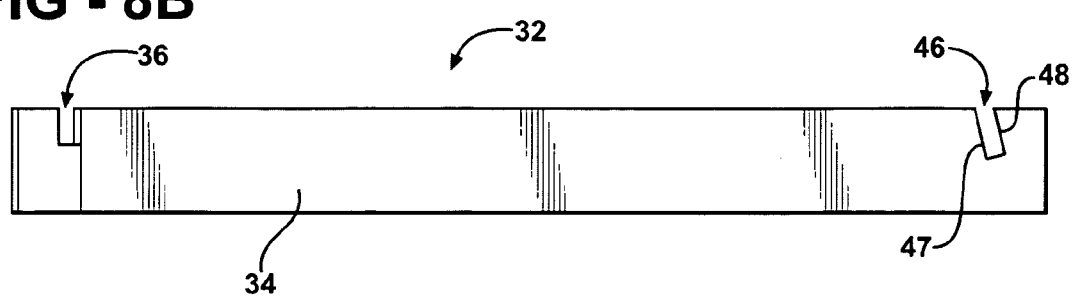
FIGS. 8A and 8B show a further embodiment of a bending tool according to the invention; and, FIG. 9 shows a combination according to the invention comprising bending arms as shown in FIGS. 8A and 8B in combination with a bone fixation device.
Figure 8A:
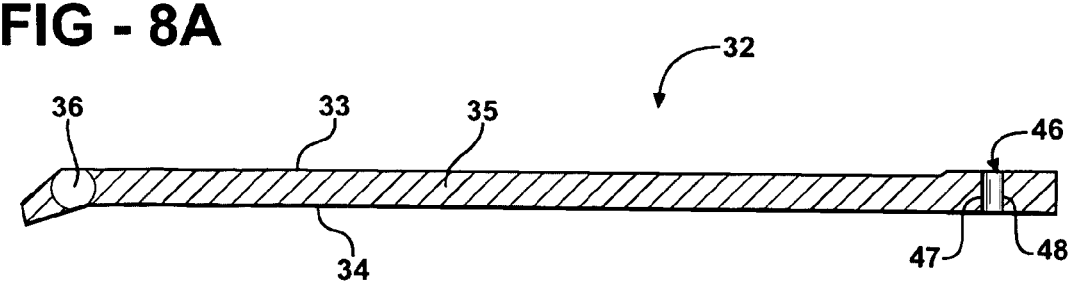

Shown in FIGS. 8A and 8B in side view is a bending arm 32 of the bending tool 30 according to the invention. The bending arm 32 of this embodiment further comprises a slot 46 remote from the recess 36. The slot 46 extends between the first and second faces 33, 34 of the bending arm 32 as shown. Planar side walls 47, 48 define the slot 46. The slot 46 extends into the side wall 35 at an angle inclined to the normal to the side wall 35. The other bending arm 31 of the bending tool 30 also includes such a slot. This slot is also inclined to the normal to the side wall 35 although the angle is different to that of the slot 46 in the first bending arm 32.

Figure 9:
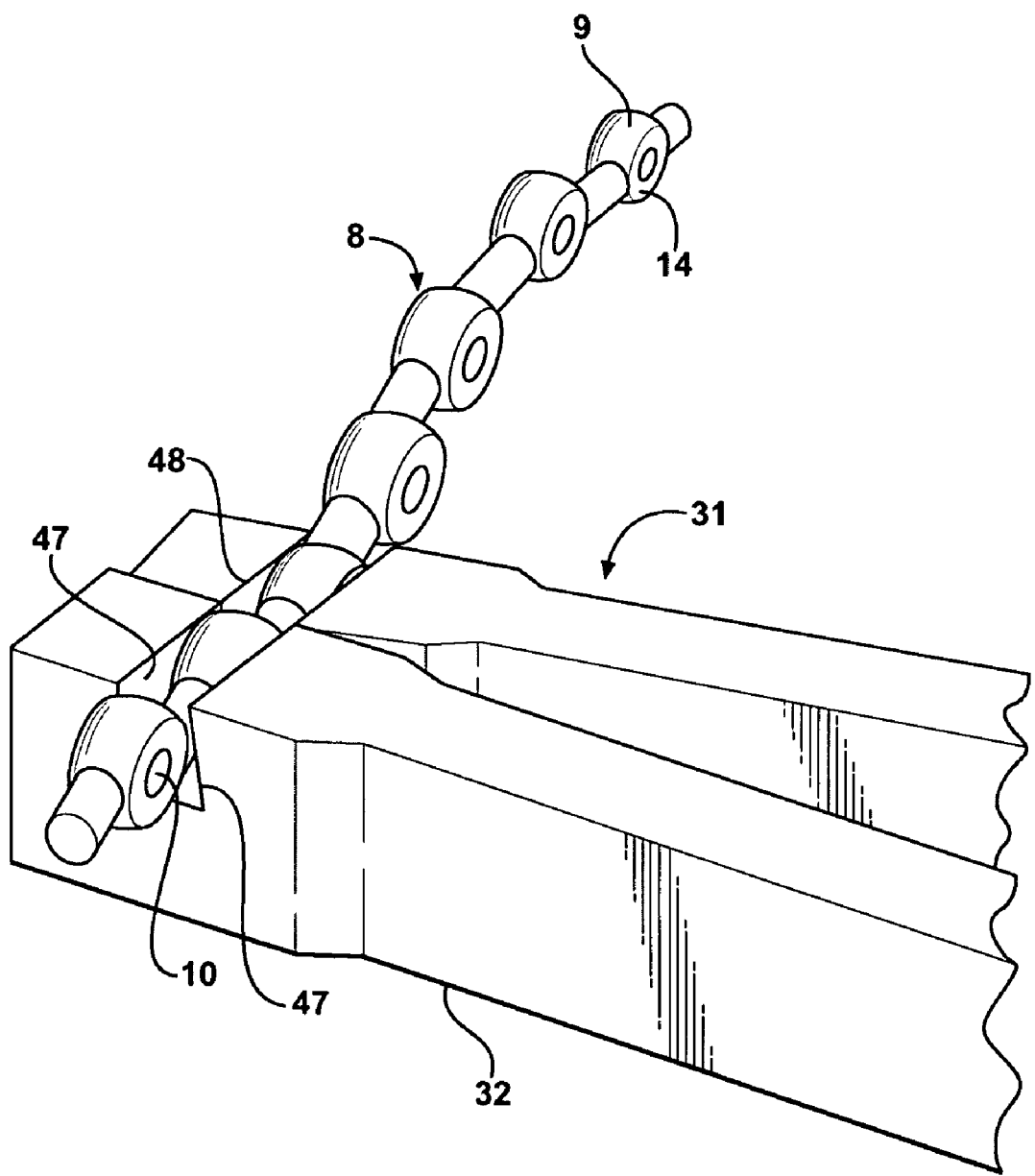

Shown in FIG. 9 are the bending arms 31, 32 of FIGS. 8A and 8B in combination with a bone fixation device 8 according to the invention. The screw receiving members 9 are frusto-spherical having flattened portions 14 around the two mouths of each screw receiving aperture 10. The two flattened portions 14 are two spaced apart planes.

The side walls 47, 48 of the slots 46 are arranged such that the screw receiving members 9 will fit into the slots 46 when the flattened portions 14 are substantially parallel to the slot side walls 47, 48. The slot side walls 47, 48 are too close together however to allow the screw receiving members 9 to rotate in the slot 46 about an axis extending between the adjacent connecting arms 12.

The slots 46 in the two arms 31, 32 are slightly mis-aligned. Accordingly, when two parallel screw receiving members 9 are arranged in the slots 46 as shown in FIG. 9 the two bending arms 31, 32 are slightly misaligned as shown. This enables a user to comfortably grip the two bending arms 31, 32. By rotating the two bending arms 31, 32 one can twist two adjacent screw receiving members 9 such that their screw receiving apertures 10 no longer lie in the same plane.

In use a surgeon first examines a bone to determine the shape of bone fixation device 8 required. The bone fixation device 8 is then bent and/or twisted into the desired shape by use of the bending tool 30. The bone fixation device 8 is then arranged in position proximate to the bone and screwed into position by bone fixation screws.

The bending of the bone fixation device 8 has been described with particular reference to bone fixation devices 8 having frusto-spherical screw receiving members 9 and bending arms 31, 32 having complementary recesses 36 and slots 46. Other shapes of bone fixation device 8 are possible, including devices having oval or ovate screw receiving members 9. Screw receiving members 9 having edges and or corners such as cubic or cylindrical are also possible although are not to be preferred. In each case the bending arms 31, 32 will have recesses 36 which have the complementary shape to the screw receiving members 9 such that the side walls 40, 41 and base of the recess 36 support the screw receiving members 9.

Screw receiving members 9 which are asymmetric about the long axis 11 of the bone fixation device 8, such as frusto-spherical screw receiving members 9 are to be preferred. Such asymmetry enables the bone fixation plate 8 to be twisted about its long axis 11 as described above.

In the embodiments shown in FIGS. 6, 8A and 8B the bending arms 31, 32 each have a step in first face 33, increasing the thickness of the bending arms remote from the recess 36. In the embodiment shown in FIGS. 8A and 8B, the slot 46 is arranged in this thicker portion. The embodiment shown in FIG. 7 includes a step in both faces 33, 34. In an alternative embodiment the faces 33, 34 do not include such a step.

What is claimed is:

1. A combination of bone fixation device and bending tool the bone fixation device comprising:
   a plurality of screw receiving members, each screw receiving member having an aperture extending therethrough for receiving a screw;
   the screw receiving members being connected together in a line by plastically deformable connecting arms extending therebetween;
   the screw receiving members being frusto-spherical and having an outer surface, said outer surface having a substantially spherical portion and a flattened portion with the flattened portion disposed around at least one mouth of the screw receiving aperture;
   a long axis extends between the screw receiving members, said outer surface of each of the screw receiving members being asymmetric about the long axis;
   the bending tool comprising first and second bending arms, each bending arm comprising:
   a first face, a second face and a side wall extending therebetween;
   the side wall comprising a recess extending between the first and second faces, an intersection of the recess with the first and second faces defining first and second connecting arm receiving apertures respectively;
   the recess being adapted to receive a screw receiving member;
   the recess between the first and second connecting arm receiving apertures being defined by inner walls, the shape of the inner walls having curved arcs that are complementary in configuration to the substantially spherical portion of the outer surface of the screw receiving member;
   the side wall further comprising a slot extending between the first and second faces, the slot being spaced from the recess along the side wall and adapted to receive a screw receiving member with the flattened portions substantially parallel to the slot side walls to prevent rotation of the screw receiving member relative to the slot about the long axis.

2. A combination as claimed in claim 1, wherein the recess in the side wall of each bending arm is arranged proximate to an end of the bending arm.

3. A combination as claimed in claim 1, wherein at least one of the bending arms has a bend along its length.

4. A combination as claimed in claim 1, wherein the screw receiving members have flattened portions around both mouths of the screw receiving apertures.

5. A combination as claimed in claim 4, wherein the flattened portions define two spaced apart parallel surfaces.

6. A combination as claimed in claim 1, wherein the slot in the side wall of each bending arm extends at an angle to the normal to the side wall.

7. A combination as claimed in claim 1, wherein the slot in the first bending arm is inclined at a different angle to the normal to the side wall to the slot in the second bending arm.

8. A combination as claimed in claim 1, wherein the slots have parallel side walls.

* * * * *